United States Patent [19]

Schep

[11] 4,345,098

[45] Aug. 17, 1982

[54] PROCESS FOR PRODUCING BENZENE CARBOXYLIC ACID SALTS AND THEIR ACIDS

[75] Inventor: Raymond A. Schep, Newport Beach, Calif.

[73] Assignee: Occidental Research Corporation, Irvine, Calif.

[21] Appl. No.: 126,143

[22] Filed: Feb. 29, 1980

Related U.S. Application Data

[63] Continuation-in-part of Ser. No. 69,466, Aug. 24, 1979, abandoned, which is a continuation of Ser. No. 883,935, Mar. 6, 1978, abandoned.

[51] Int. Cl.³ .................. C07C 51/02; C07C 51/353; C07C 51/487
[52] U.S. Cl. .................................. 562/482; 562/407; 562/408; 562/479; 562/480; 562/481; 562/485
[58] Field of Search ............... 562/481, 480, 482, 485, 562/407, 408, 479

[56] References Cited

U.S. PATENT DOCUMENTS

| | | | |
|---|---|---|---|
| 2,171,871 | 9/1939 | Walker | 260/515 |
| 2,176,348 | 4/1939 | Juettner | 260/515 |
| 2,193,337 | 3/1940 | Leicester | 260/538 |
| 2,461,740 | 2/1949 | Kiebler | 260/515 |
| 2,555,410 | 6/1951 | Howard | 260/515 |
| 2,762,840 | 9/1956 | Howard | 260/525 |
| 2,785,198 | 3/1957 | Grosskinsky et al. | 260/525 |
| 2,786,074 | 3/1957 | Goren | 260/514 |
| 2,819,300 | 1/1958 | Grosskinsky et al. | 260/515 |
| 2,833,816 | 5/1958 | Saffer et al. | 260/524 |
| 2,927,130 | 3/1960 | Schutt | 260/525 |
| 2,948,750 | 8/1960 | Blaser et al. | 260/515 |
| 2,981,751 | 4/1961 | Keith et al. | 260/524 |
| 3,023,216 | 2/1962 | Blaser et al. | 260/295.5 |
| 3,023,217 | 2/1962 | Stein et al. | 260/295.5 |
| 3,042,717 | 7/1962 | Schenk | 562/479 |
| 3,064,043 | 11/1962 | Taylor et al. | 260/523 |
| 3,064,046 | 11/1962 | Taylor et al. | 260/523 |
| 3,093,683 | 6/1963 | Raecke et al. | 522/479 |
| 3,215,735 | 11/1965 | Sakurai et al. | 260/525 |
| 3,247,246 | 4/1966 | Fragen | 562/482 |
| 3,259,650 | 7/1966 | Decker et al. | 260/515 |
| 3,468,943 | 9/1969 | Creighton et al. | 260/523 |
| 3,529,020 | 9/1970 | Landis et al. | 260/524 |
| 3,558,458 | 1/1971 | Bloch | 260/158 |
| 3,579,572 | 5/1971 | Amedjian et al. | 260/515 |
| 3,702,340 | 11/1972 | Selin et al. | 260/515 H |
| 3,709,931 | 1/1973 | Proell et al. | 260/515 H |
| 3,766,258 | 10/1973 | Engelbrecht et al. | 260/515 P |

OTHER PUBLICATIONS

Bearse, E. A. et al., "Production of Chemicals by Oxidation of Coal", A Battelle Energy Program Report, Mar. 31, 1975.
Franke, N. W. et al., "Water-Soluble Polycarboxylic Acids by Oxidation of Coal", Ind. and Eng. Chemistry, vol. 44, p. 2791, (1952).
U.S. Bureau of Mines Information Circular No. 8234, pp. 74–98.
Ogata, Yoshiro et al., "The Preparation of Terephthalic Acid from Phthalic or Benzoic Acid", J. Am. Chem. Soc., vol. 79, pp. 6005–6008.
Chin, Yu-Ren, "Terephthalic Acid from Toluene via Dipotassium Terephthalate", Stanford Research Institute Report No. PEP'76-2-3, Feb. 1977, (pp. 1–16).

*Primary Examiner*—Natalie Trousof
*Assistant Examiner*—Vera C. Clarke
*Attorney, Agent, or Firm*—Forrest E. Logan

[57] ABSTRACT

A process for producing an isomerized benzene carboxylic acid salt by treating a mixture of an aromatic material, water, and a water soluble reagent comprising a Group Ia or IIa metal with oxygen under conditions sufficient to convert at least a portion of the aromatic material to a benzene carboxylic acid salt of the metal; isomerizing the benzene carboxylic acid salt by heating without converting the benzene carboxylic acid salt to a benzene carboxylic acid salt of a different Group Ia or IIa metal prior to isomerizing; and recovering the benzene carboxylic acid salt. Another embodiment further comprises converting the isomerized benzene carboxylic acid salt to isomerized benzene carboxylic acid; regenerating the reagent; recovering the isomerized benzene carboxylic acid; and recycling the reagent thusly regenerated to supply a portion of the reagent required for producing the benzene carboxylic acid salt. In one embodiment the water soluble reagent is potassium carbonate, or potassium bicarbonate or mixtures thereof. In one embodiment a benzene carboxylic acid salt is produced from carbonaceous material having a high degree of aromaticity.

23 Claims, 2 Drawing Figures

PROCESS FOR PRODUCING BENZENE CARBOXYLIC ACID SALTS AND THEIR ACIDS

This is a continuation-in-part application of Ser. No. 69,466 filed Aug. 24, 1979, now abandoned, which was a continuation of Ser. No. 883,935 filed Mar. 6, 1978 now abandoned.

TECHNICAL FIELD

The field of the invention relates to the production of benzene carboxylic acids from aromatic materials, such as coal, petroleum residium, shale oil, and tar sands. The invention is particularly useful for the production of terephthalic acid from bituminous coal.

BACKGROUND ART

U.S. Pat. No. 2,785,198 discloses a process for producing polycarboxylic acids from bituminous coal, lignites, peat and the like or their carbonization product such as coal, tar, or pitch by thermal treatment with oxidizing agents such as nitric acid, chromic acid, permanganate, or oxygen or air under super-atmospheric pressure in an alkaline medium.

The crude oxidation product is subject to an extraction treatment with a polar organic solvent for both the monocyclic aromatic and high molecular weight polycarboxylic acids, and treating the thusly formed solution with water to extract the monocyclic aromatic polycarboxylic acids from the remainder of the mixture. The alkaline medium disclosed is sodium hydroxide.

U.S. Pat. No. 2,193,337 discloses a process for producing organic acids by heating carbonaceous material such as sawdust, wood chips, peat, or coal with oxygen-containing gases at elevated pressures and temperatures in the presence of at least 10 times the weight of the carbonaceous material of water and preferably an oxide or hydroxide of an alkali or alkaline earth metal. Oxalic acid and other organic acids which are formed, such as mellitic and benzoic acid or acetic acid, may be isolated from the resulting reaction mixture as salts of the alkali or alkaline earth metals. The caustic material disclosed is an oxide or hydroxide of an alkali metal or an alkaline earth metal and specifically lime, quick-lime, and caustic soda.

U.S. Pat. No. 2,786,074 discloses a process for making organic acids by oxidizing carbonaceous materials at elevated temperatures and pressures with gaseous oxygen in the presence of an alkaline solution. Alkalis which are suitable for use in a high pressure reactor are specified as sodium hydroxide, potassium hydroxide, and mixtures thereof.

U.S. Pat. No. 2,461,740 discloses a process for oxidizing carbonaceous material to aromatic acids using a two-stage oxidation process.

In the first stage, the carbonaceous material is oxidized to a state where it is soluble in aqueous alkali such, for example, as a solution of sodium hydroxide, potassium hydroxide, sodium carbonate, or potassium carbonate, especially at elevated temperatures.

Any acid or acid anhydride with suitable oxidizing properties which can be regenerated by air and recycled in the process can be employed, for example sulfur trioxide, oxides of nitrogen, or the acids formed by reaction of these compounds with water. Specifically disclosed are sulfur trioxide, $N_2O_3$, and $N_2O_5$.

In the second stage, U.S. Pat. No. 2,461,740 discloses the use of a high pressure elevated temperature reaction of oxygen gas in aqueous alkali. The aqueous alkali employed is a solution of sodium hydroxide, potassium hydroxide, sodium carbonate, or potassium carbonate.

U.S. Pat. No. 3,023,217 discloses a process for introducing carboxyl groups into aromatic compounds free from carboxyl groups, such as aromatic carbocyclic hydrocarbons and aromatic heterocyclic hydrocarbons. The patent discloses a process for introducing into aromatic carbocyclic or aromatic heterocyclic compounds free from carboxyl groups by reacting such materials in the absence of substantial amounts of oxygen, such as a non-oxidative atmosphere and under anhydrous conditions, with alkali metal salts of aliphatic carboxylic acids at elevated temperatures and pressures in the presence of catalysts. As disclosed in the process, it is necessary to exclude the presence of substantial quantities of oxygen. Examples of aliphatic carboxylic acids which are used in the form of their alkali metal salts, especially their potassium salts, are oxalic acid, malonic acid, maleic acid, and trichloroacetic acid.

Examples of suitable compounds free from carboxyl groups which may be used as starting materials for the process are aromatic carbocyclic compounds free from carboxyl groups such as monocyclic aromatic hydrocarbons such as benzene or its derivatives having saturated alkyl or cycloalkyl substitutes attached thereto, and dicyclic aromatic hydrocarbons such as naphthalenes, diphenyl, and other polycyclic aromatic hydrocarbon compounds. Similarly, aromatic heterocyclic compounds free from carboxyl groups which may be used as starting materials are heterocyclic compounds which contain one or more heteroatoms in the ring and which are designated as having an aromatic character because of their chemical behavior.

U.S. Pat. No. 2,948,750 discloses a process for carboxylating aromatic hydrocarbons by direct introduction of carbon dioxide to produce polycarboxylic acids.

Suitable starting materials which are disclosed are aromatic hydrocarbons, especially benzene but also toluene, xylene, cumene and diisopropyl benzene and other benzenes substituted with saturated or unsaturated alkyl or cycloalkyl radicals, naphthalene, diphenyl, diphenylmethane and other aromatic compounds which may also be substituted with hydrocarbon radicals.

Selective carboxylation is accomplished by heating the starting materials in the presence of an acid-binding agent, and carbon dioxide under anhydrous conditions. Examples of the acid-binding agent are carbonates of alkali metals, especially potassium carbonate, the salts of other weak acids such as bicarbonates, formates, or oxalates. Similarly, the corresponding compounds of other metals are suitable; for example, the carbonates of the alkali earth metals.

U.S. Pat. No. 3,023,216 discloses a method of introducing carboxyl groups into aromatic carbocyclic compounds free from carboxyl groups by reacting these compounds in a non-oxidative atmosphere with alkali metal salts of aromatic carbocyclic or aromatic heterocyclic carboxylic acids.

Suitable compounds which are free from carboxyl groups which may be used as starting compounds in this patent are similar to the starting compounds in U.S. Pat. No. 2,948,750.

U.S. Pat. No. 3,023,216 discloses reacting aromatic carboxylic compounds free from carboxyl groups with aromatic carboxylic acids in the form of their alkali metal salts.

Both U.S. Pat. Nos. 3,023,216 and 2,948,750 require specific chemical compounds as starting materials.

U.S. Pat. No. 2,833,816 discloses a process for oxidizing aromatic compounds using a catalyst comprising a lower aliphatic carboxylate salt of a heavy metal and bromine. Examples of a heavy metal are manganese, cobalt, nickel, chromium, vanadium, molybdenum, tungsten, tin, and cerium.

The metals may be supplied in the form of metal salts; for example such as manganese acetate. The bromine may be supplied as ionic bromine, or other bromine compounds soluble in the reaction medium such as potassium bromate.

Thus, the process requires the conjoint presence of bromine and a heavy metal oxidation catalyst.

The starting material required is an aromatic compound containing one or more aliphatic substituents to produce corresponding aromatic carboxylic acids.

U.S. Pat. No. 3,064,043 discloses a process for oxidizing para-toluic acid or para-formyl toluene to produce terephthalic acid.

U.S. Pat. No. 3,064,046 discloses a process for oxidizing toluic acid or formyl toluene to produce orthophthalic acid or isophthalic acid.

Both U.S. Pat. Nos. 3,064,043 and 3,064,046 require specific starting materials to be oxidized.

U.S. Pat. No. 3,558,458 discloses a process for preparing aromatic acids by treating an alkyl aryl ketone with water at an elevated temperature in the presence of a reaction promoting agent. The reaction promoting agent may comprise an alkaline catalyst, a transition metal salt, or actinic light. Examples of an alkaline catalyst include potassium acetate, lithium acetate, rubidium acetate, and cesium acetate. The process is conducted in water at a temperature of about 200° to 400° C.

The art discloses processes for the alkaline oxidation of coal employing large amounts of chemicals relative to the amount of water soluble coal acids prouced, see U.S. Pat. No. 2,786,074 and a report entitled "Producton of Chemicals by Oxidation of Coal", Battelle Laboratory, Columbus, Ohio of Mar. 31, 1975. The report also suggests the use of potassium acetate and acetic acid in a cyclic process for the Henkel reaction at page 19. The substance of the Battelle Report is incorporated herein by reference.

Recovery of caustic soda and sodium carbonate was disclosed by Industrial and Engineering Chemistry, Volume 44 (1952) at page 2791 in an article entitled "Water-Soluble Polycarboxylic Acids by Oxidation of Coal" beginning at page 2784.

Japanese patent disclosure 18,365 discloses the reclamation of alkali by recrystallization and requires the consumption of one part by weight of alkali and 1.5 parts of sulfuric acid for each two parts of coal consumed.

Non-alkaline oxidation of coal generally yields about 10 parts by weight of water soluble coal acids based on 100 parts of coal carbon consumed. Alkaline oxidation yields have been about 30 to about 42 parts per 100 parts of coal carbon consumed. Therefore, alkaline oxidation processes are favored because of the higher yield possible.

In systems like $HCl/KCl$, $H_2SO_4/K_2SO_4$, and $HNO_3/KNO_3$ the salts do not produce an alkali solution by hydrolysis because the acids involved are too strong. These systems over oxidize the coal and therefore result in much lower yield of coal acids.

Another disadvantage of treatment of coals with strong acids is the production of unwanted by-products by chlorination, sulfation, or nitration of the aromatic nuclei of the coal.

Coal acids have been prepared by nitric acid oxidation, U.S. Pat. Nos. 3,468,943; 3,709,931; 2,555,410; in the presence of nitrogen catalyst, U.S. Pat. No. 3,702,340; and oxidation in a non-alkaline aqueous medium, U.S. Pat. No. 3,259,650.

The caustic-oxygen treatment of coal has been described in U.S. Bureau of Mines Information Circular No. 8234 at pages 74 to 98.

In another process, U.S. Pat. No. 3,259,650 discloses the use of a non-alkaline medium and produces lower yields of water soluble coal acids.

U.S. Pat. No. 2,927,130 discloses a process for the recovery of alkalis and terephthalic acid from aqueous solutions containing alkali salts of terephthalic acid. Alkalis of interest are sodium, potassium and ammonium. The patent discloses that dialkali salts of terephthalic acid in aqueous solution can easily be divided into difficulty soluble monoalkali salts and alkali bicarbonate by introducing carbon dioxide into the solution, and that the difficulty soluble monoalkali salts of terephthalic acid can be hydrolyzed with water into free terephthalic acid and dialkali salts of terephthalic acid. The free terephthalic acid separates out as a solid, while the dialkali terephthalate remains in solution. U.S. Pat. No. 2,927,130 is incorporated herein by reference.

U.S. Pat. No. 2,819,300 discloses a process for oxidizing carbonaceous material with nitric acid, and then oxidizing the oxidation products produced from the nitric acid-carbonaceous material reaction with sulfuric acid to complete the oxidation to benzene carboxylic acids.

Although oxidation can be carried out in reclaimable acidic media, these processes are not as desirable because of lower yields and unwanted by-products due to chlorination, sulfation, and nitration.

The art discloses a process for preparing terephthalic acid by heating pure potassium phthalate, or pure potassium isophthalate, or pure potassium benzoate in the presence of catalyst such as cadmium, zinc and other metals, as reported in the Journal of American Chemical Society, Volume 79, pages 6005 to 6008.

The art also discloses a catalytic process for preparing terephthalic acid from toluene by oxidizing toluene to benzoic acid, reacting the thusly formed benzoic acid with potassium terephthalate in a methathesis reaction to produce terephthalic acid and potassium benzoate, and heating the thusly formed potassium benzoate in the presence of a catalyst to produce potassium terephthalate and benzene by a disproportionation reaction. Terephthalic acid and benzene are recovered and the thus formed potassium terephthalate is recycled to the methathesis reaction. The process is reviewed in Stanford Research Institute Report No. PEP'76-2-3 of Feb., 1977.

U.S. Pat. No. 3,215,735 discloses a process for treating a solution containing dialkali terephthalate and non-terephthalic acid as impurities with a reagent to adjust the pH of the solution so that terephthalic acid is in a soluble form while essentially all of the non-terephthalic acid is in an insoluble filterable form.

U.S. Pat. No. 3,579,572 discloses a process for the production of terephthalic acid which comprises treating an aqueous lithium or magnesium terephthalate solution with carbon dioxide under pressure, at a temperature between its solidification temperature and 80° C., and separating the terephthalic acid which precipitates.

U.S. Pat. No. 3,766,258 discloses a process for the catalytic carboxylation of an alkali metal aromatic carboxylate to an acid containing at least one more carboxyl group.

U.S. Pat. No. 2,171,871 discloses that alkali metal derivatives of organic acid salts may be reacted with various reagents reactive with alkali metal organic compounds, e.g., carbon dioxide, sulfur dioxide or organic halides, to produce valuable products.

U.S. Pat. No. 2,176,348 discloses a process for preparing mellitic acid by a two-step oxidation of coal. The coal is first treated with a suitable oxidizing acid with or without the presence of a catalyst, followed by oxidation with an oxidizing salt such as alkaline permanganate.

U.S. Pat. No. 2,762,840 discloses that polycarboxy aromatic acids can be prepared by controlled oxidation with oxygen gas of an aqueous, alkaline suspension of bituminous coal.

U.S. Pat. No. 2,981,751 is directed toward a process for the oxidation of substituted aromatic compounds having at least one aliphatic, cycloaliphatic or partially oxidized aliphatic or cycloaliphatic substituent attached to the aromatic nucleus in the presence of an oxygen-containing gas and a calcined solid oxidation catalyst. The substituted aromatic feed materials disclosed are toluene, butylbenzene, xylene, cumene, durene, dibutylbenzene, acetophenone, propiophenone, benzaldehyde, tolualdehyde, Tetralin, para-xylene, and cumene hydroperoxide. The oxidation is in the presence of a calcined solid oxidation catalyst which is derived by calcining an inorganic base having deposited thereon catalytic amount of a promoting metal component.

U.S. Pat. No. 3,529,020 discloses a process for oxidizing an organic material in the presence of a heavy metal crystalline aluminosilicate having uniform pores sufficiently large to permit entry of at least a portion of the organic material, and an oxidation initiator which is present in the pores. The heavy metal crystalline aluminosilicate acts as a catalyst.

The use of the applicant's invention allows reclamation of the reagent, higher yields, and less production of undesirable by-products. In the applicant's invention, the material principally consumed in the process is the aromatic material. Almost all other reagents are almost fully recoverable and completely reusable. In one embodiment of the applicant's invention, the applicant has found that 92 to 95 percent by weight of potassium could be recovered as potassium acetate.

SUMMARY AND DISCLOSURE OF THE INVENTION

The invention provides an improved process for the production of benzene carboxylic acid salts and their acids from carbonaceous materials containing some aromaticity.

A mixture of carbonaceous material, water, and a water soluble reagent comprising a Group Ia or IIa metal is first formed. The water soluble reagent, comprising a Group Ia or IIa metal is such that it will produce an alkaline solution by hydrolysis. Thus, hydrogen is excluded from the group comprising Group Ia or IIa metals.

In one embodiment the reagent is a formate, acetate, or propionate. Examples of such soluble reagents are potassium acetate, potassium formate, potassium propionate, sodium acetate, sodium formate, sodium propionate, lithium acetate, lithium formate, lithium propionate, magnesium acetate, calcium acetate, barium acetate, beryllium acetate, etc.

The carbonaceous material may be coal, lignite, peat, coke, char, and other materials containing or capable of evolving, or producing, a hydrocarbon material, either liquid or solid during an alkaline aqueous oxidation treatment as described below.

Pure water is not required and in fact process water may be used over and over at least in part.

The mixture can be formed in any manner in a mixing zone using mixers suitable for handling slurries containing solids if a solid or solid-like carbonaceous material is to be converted, or mixers suitable for handling liquids if liquid aromatic materials are to be converted.

The mixture is removed from the mixing zone and fed to a reaction zone wherein the mixture is reacted with oxygen, or an oxygen-containing gas such as air. The reaction zone and the mixing zone can be, if desired, in the same vessel as in some batch-type processes, or they may be separate vessels as in some continuous processes.

More particularly, this invention provides an improved process for the production of benzene carboxylic acids from carbonaceous materials which contain a high degree of aromaticity of a quality suitable for the production of benzene carboxylic acids. A pure carbonaceous material is not required, and in fact, the process is particularly suitable for naturally occurring carbonaceous materials which are a mixture of structurally complex molecules such as coal or coal derived substances which also are structurally complex.

A mixture of an aromatic material, water, and a water soluble reagent comprising a Group Ia or IIa metal, such as a metal formate, acetate, or propionate is first formed. As described above, the Group Ia or IIa metal formate, acetate, or propionate is such that it will produce an alkaline solution by hydrolysis.

Other alkaline substances, however, will work as the water soluble reagent such as for example potassium carbonate.

The aromatic material may be coal, especially bituminous coal, petroleum residium, lignite, peat, pitch, tar, coke, char, oil shale, oil from oil shale, and any other material containing or capable of evolving or producing aromatic material either liquid or solid.

Any kind of coal, including lignite, anthracite, or coke or char can be used, but bituminous coals give the best benzene carboxylic acid yields because of the particular quality of their aromaticity. Yields of benzene carboxylic acid from anthracite coal are low because the quality of the aromaticity in anthracite is too polynuclear. Anthracitic coals produce a product having a high percentage of polynuclear aromatic acids rather than benzene carboxylic acids.

Yields from lignites are low because lignite produces little aromatic material, thus the yield of benzene carboxylic acids will be low.

The mixture is treated with oxygen under conditions sufficient to convert the aromatic material to a benzene carboxylic acid salt of the reagent. In general, a temperature of about 200° to about 350° C. is required. The pressure in the reaction zone should be sufficient to maintain a liquid state in the reaction zone. Generally this requires a pressure of at least about 250 psig. Preferred reaction zone conditions are about 270° C. and about 900 psig.

Reaction times in the reaction zone depend upon the temperature, degree of agitation, the proportion of aromatic material, water, and water soluble reagent, the solid-to-liquid ratio, and the particle size of the solid material. Generally, reaction times of from about ten minutes to about three hours are required.

In one embodiment, during oxidation benzene carboxylic acids are formed which react with the reagent to form benzene carboxylic acid salts, and the volatile acid of the reagent, the latter of which can be reclaimed by venting vapor from the reactor.

After treating the mixture with oxygen or an oxygen-containing gas such as air to convert the aromatic material into benzene carboxylic acid, water is removed from the mixture in a dewatering zone. In the dewatering zone, an amount of water is removed which is sufficient that upon the addition of "an acid of said reagent" that at least a portion of the benzene carboxylic acid salt will be converted to a benzene carboxylic acid precipitate. The solution will contain the regenerated reagent which can be recycled for further use. Several treating steps can be used to separate higher polynuclear aromatic and humic acids first.

As used herein and claimed herein, the expression "an acid of the reagent" means an acid which is formed by the replacement of the Group Ia or IIa metal atom of the water soluble reagent with hydrogen. The acid, therefore, will be formic, acetic, or propionic acid in the embodiments utilizing potassium formate, acetate, or propionate as the water soluble reagent, respectively.

Thus the invention can be seen to comprise the use of an alkaline-acid-system. Examples of alkaline-acid systems which may be used in the invention are potassium acetate-acetic acid, or potassium formate-formic acid, or potassium propionate-propionic acid. Any alkaline-acid buffer system can be used from which a component is volatile or extractable. Since potassium acetate is the most soluble of the above three, it is therefore preferred over the other two.

As mentioned earlier, systems like HCl/KCl, $H_2SO_4/K_2SO_4$, and $HNO_3/KNO_3$ are unsuitable because the salts do not produce an alkali solution by hydrolysis since the acids involved are too strong. Equally important is the fact that unwanted by-products are formed by chlorination, sulfation, or nitration of aromatic nuclei.

The dewatering zone can be in the same vessel as the reaction zone as in some batch processes, or it can be in a separate vessel as in some continuous processes.

The water from the dewatering zone can be used in the mixing zone to supply at least part of the water requirements in the mixing zone.

The dewatered mixture, i.e., the mixture from the dewatering zone, is then treated in an acidification zone with an acid of the reagent to convert the aromatic carboxylic acid salt to an aromatic carboxylic acid precipitate and the reagent. For example, potassium phthalate treated with acetic acid is converted to phthalic acid and potassium acetate. In the case where no aromatic carboxyic acid precipitate is formed separation can be achieved by solvent extraction or other suitable means.

The acidification zone may be in the same vessel as the dewatering zone as in some batch processes, or it can be in a separate acidification vessel as in some continuous processes. Sufficient acid must be added to the mixture to effect the conversion of the benzene carboxylate to the benzene carboxylic acid and to cause precipitation. Polynuclear and humic acid may be removed before precipitation of the benzene carboxylic acid.

The conditions in the acidification zone must be such that the species of benzene carboxylic acid desired to precipitate will in fact precipitate. These conditions, especially temperature, will vary depending upon the species or species of benzene carboxylic acids which are desired to form precipitates.

After forming the benzene carboxylic acid precipitate, the precipitate is separated from the mixture in a separation zone. Any apparatus capable of separating solids from liquids may be used such as a filter. The separated solid comprises the benzene carboxylic acid precipitate.

The separated liquid from the separation zone is treated in a regeneration zone to recover the reagent from the liquid.

The liquid stream from the acidification zone contains both the reagent and an acid of the reagent. The reagent and the acid of the reagent are separated in a separation zone. The separated reagent can be used for additional treatment of fresh aromatic material in the mixing zone whether the process is batch or continuous.

The separated acid of the reagent can be used to acidify additional material in the acidification zone whether the process is batch or continuous.

In another embodiment an isomerized benzene carboxylic acid salt is produced by treating a mixture of an aromatic material, water, and a water soluble reagent comprising a Group Ia or IIa metal, the reagent is such that it produces an alkaline solution by hydrolysis, with oxygen under conditions sufficient to convert at least a portion of the aromatic material to a benzene carboxylic acid salt of the Group Ia or IIa metal of the reagent. The benzene carboxylc acid salt is isomerized by heating to produce an isomerized benzene carboxylic acid salt without converting the benzene carboxylic acid salt to a benzene carboxylic acid salt of a different Group Ia or IIa metal prior to isomerizing the benzene carboxylic acid salt. Thus, for example, a sodium salt of the benzene carboxylic acid is not converted to a potassium salt of the benzene carboxylic acid. In a further embodiment, the isomerized benzene carboxylic acid salt is then converted to an isomerized benzene carboxylic acid, and the reagent comprising said Group Ia or IIa metal is regenerated. The isomerized benzene carboxylic acid is recovered and the reagent comprising the Group Ia or IIa metal thusly regenerated is recycled to supply a portion of the reagent required for producing the benzene carboxylic acid salt.

The process is particularly valuable where the said aromatic material is coal and/or the reagent is a potassium reagent such as for example potassium carbonate.

DESCRIPTION OF PREFERRED EMBODIMENT

Figure 1:
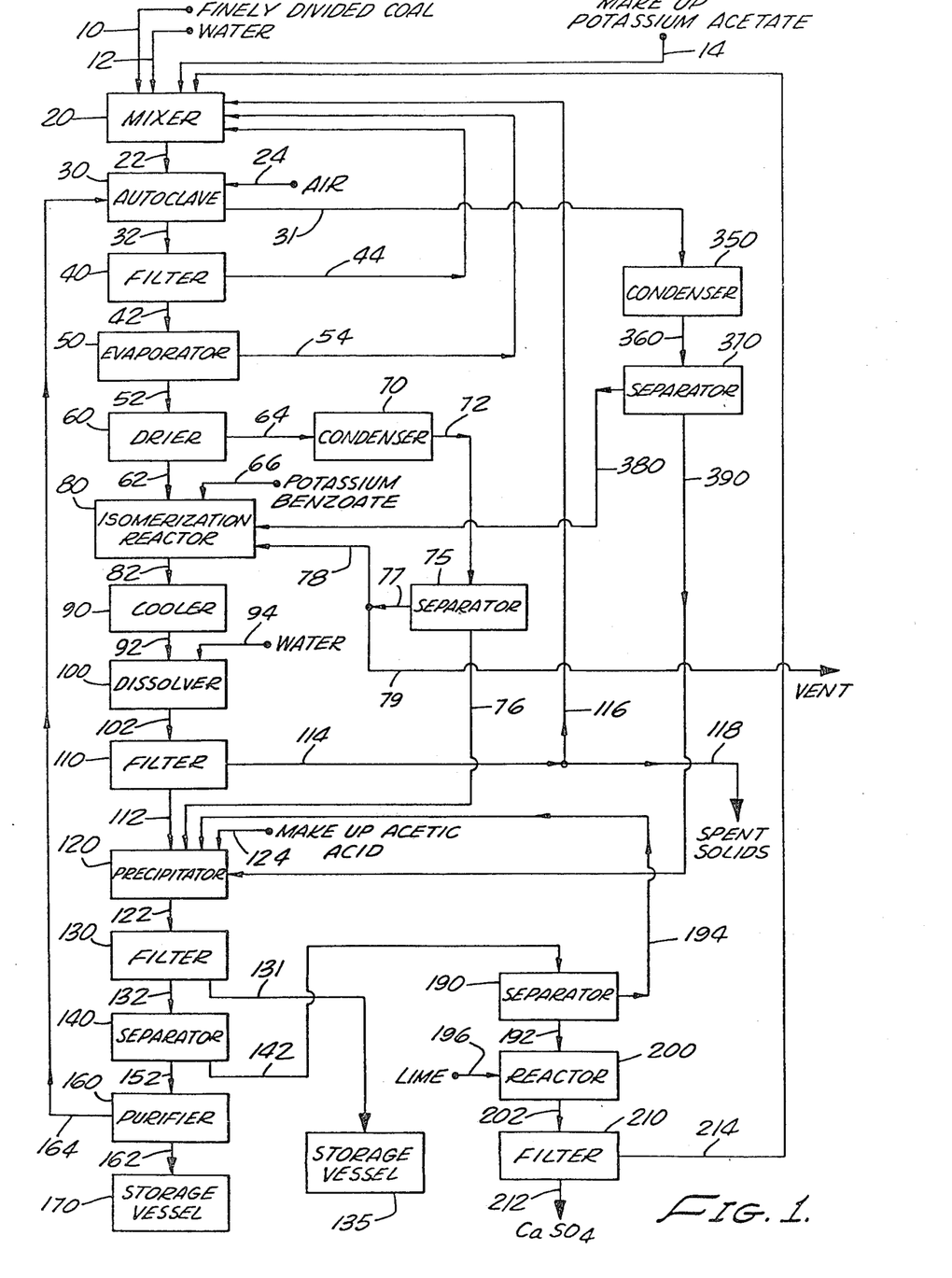
FIG. 1 is a schematic flow diagram for my process for the production of terephthalic acid from bituminous coal.

Referring to FIG. 1, a finely divided bituminous coal through stream 10, water through stream 12 and potassium acetate through stream 14 are introduced into mixer 20. About five parts water by weight and about 1 to 5 parts by weight of potassium acetate are added to the mixer per part by weight of coal. Any type of mixer may be used. After mixing, the mixture is removed from mixer 20 through stream 22 and introduced into autoclave 30. Air or oxygen is introduced into autoclave 30 through line 24. About two parts by weight of oxygen per part by weight of coal is charged to autoclave 30.

The coal is oxidized in autoclave 30 to produce aromatic carboxylic acids comprising benzene carboxylic acids, polynuclear aromatic acids, carbon dioxide and water. The potassium acetate reacts with the thusly formed acids to produce potassium salts thereof and acetic acid.

The autoclave is operated at a temperature of about 200° to about 350° C. preferably about 270° C., and at a pressure of about 250 to about 2000 psig, preferably about 900 psig. Temperatures below about 200° C. are not desirable because the formation of polynuclear aromatic carboxylic acids are favored and temperatures above about 350° C. are not desirable because the formation of carbon dioxide is favored. Pressures outside this range, however, can be used. Lower pressures are not desirable because kinetic rates are lower. Higher pressures are not desirable because of the cost of high pressure equipment and compression costs. Preferably the contents of autoclave 30 are agitated to increase product yield and to lower reaction time.

Gases comprising carbon dioxide, acetic acid and water vapor are removed from autoclave 30 through line 31 and fed into condenser 350. In condenser 350 the vaporous acetic acid and water vapor are condensed. The condensate and gases are removed from condenser 350 through line 360 and fed to separator 370. The condensate comprising aqueous acetic acid is separated from the gas comprising carbon dioxide in separator 370. The gas is removed from separator 370 through line 380 and the condensate through line 390. Both of streams 380 and 390 are fed to subsequent steps in the process as will be described later.

The thusly formed aromatic acid salts are discharged from autoclave 30 through line 32 to filter 40.

Filter 40 is used to separate the liquid product from residual solids. Filter 40 may be any type of filter, such as a precoated revolving drum filter or a vacuum filter. The liquid product containing the dissolved thusly formed potassium acid salts is removed from filter 40 through line 42. The solids which contain unreacted coal and ash are removed from filter 40 through line 44 and recycled to mixer 20. The filration step is optional and is not needed if the solids in stream 32 will not interfere with a subsequent isomerization step as described later.

Liquid stream 42 from filter 40 is charged to evaporator 50 where most of the water therein is removed. The damp solids containing the thusly formed potassium acid salts are removed from the evaporator 50 through line 52 and enter dryer 60. Water from evaporator 50 is removed through line 54 and recycled to mixer 20.

In dryer 60, the remaining water which contains acetic acid is removed from the damp solids. The thusly formed dry solids are removed from dryer 60 through line 62 and charged to isomerization reactor 80. It is important to dry the solids charged to the isomerization reactor sufficiently to prevent excessive reaction between water and aromatic carboxylic acids in the isomerization reactor.

In an alternate embodiment, potassium benzoate can be introduced, as through line 66, into isomerization reactor 80 to simultaneously undergo conversion to terephthalic acid.

In isomerization reactor 80, the dry acid salts are catalytically isomerized at a temperature of from about 400° to about 440° C. at a pressure of about 10 atmospheres, and for a period of time of about 10 to about 100 minutes to cause isomerization of the dry potassium acid salts to more valuable products such as terephthalate and isomerized polynuclear aromatic acid salts.

Preferably a carbon dioxide environment is maintained in the isomerization reactor. Especially preferably the carbon dioxide is produced in the oxidation step as mentioned earlier and is fed to the isomerization reactor 80 through line 380. If free oxygen is present in the gas in line 380 then it must be removed or converted to carbon dioxide (not shown) before the gas is fed to isomerization reactor 80. Stream 380 may be used as a source of carbon dioxide without any subsequent purification or treatment, if it does not contain free oxygen, since it is not necessary to use pure carbon dioxide. In still another embodiment, any inert atmosphere, such as nitrogen, may be used.

Examples of catalysts useful for promoting the isomerization are the oxides, carbonates, or halides of zinc or cadmium. Organic salts, particularly carboxylates such as cadmium benzoate, are particularly good catalysts. Cadmium iodide is a preferred catalyst, in concentrations varying from 1 to 15 parts by weight per 100 parts by weight of aromatic carboxylic acid salts. The preferred concentration of cadmium iodide is about 5 parts by weight per 100 parts by weight of the aromatic carboxylic acid salt mixture.

The products are removed from isomerization reactor 80 through line 82 and enter cooler 90 where the products are cooled to a temperature of about 200° to about 100° C. preferably about 100° C. It is necessary to cool the products because decomposition occurs at higher temperatures when exposed to water or oxygen. For example, exposure to water can cause potassium terephthalate to decompose to benzoic acid and potassium bicarbonate; and exposure to oxygen can cause potassium terephthalate to decompose to carbon dioxide and potassium bicarbonate.

The cooled products removed from cooler 90 through line 92, together with water, which can contain dissolved therein dipotassium terephthalate from line 94, are charged to dissolver 100. In dissolver 100 the potassium acid salts are completely dissolved.

The mixture is removed from dissolver 100 through line 102 and enters filter 110 where any undissolved solids are separated from the liquid portion of the mixture. The thusly separated liquid portion is removed from filter 110 through line 112 and charged to precipitator 120. Treatment of the solution with activated charcoal to remove any impurities which impart a color to the terephthalic acid solution can be performed prior to the precipitation step if desired.

The thusly separated solids, which consist essentially of char and ash, are removed from filter 110 through line 114 and a portion thereof is recycled to mixer 20 by way of line 16, or alternately the solids are recycled to autoclave 30 (not shown), to undergo further oxidation to produce additional carboxylic acids. In order to prevent buildup of solids, principally ash, in the system, another portion of the solids is removed from the system through line 118.

In still another embodiment (not shown), solids from filter 110 are mechanically treated or floated to separate the ash material from the carbonaceous material. The carbonaceous material can be returned to mixer 20, or alternately to autoclave 30, while the separated ash fraction is removed from the system.

Returning to dryer 60, the vapor stream, removed from the dryer through line 64, is fed to condenser 70 whereupon water vapor containing acetic acid vapors is condensed to produce aqueous acetic acid. The condensate and any gases are removed from condenser 70 through line 72 and fed to separator 75 which separates the aqueous acetic acid from the gases. The separated aqueous acetic acid is removed from separator 75 through line 76 and then charged to precipitator 120. Make-up acetic acid is fed to precipitator 120 through line 124. An excess of acetic acid is maintained in the precipitator to effect precipitation of terephthalic acid. A pH of about 3 to about 7, preferably about 4.7 to about 5.5, is maintained in precipitator 120 to cause conversion of the potassium terephthalate to the terephthalic acid. By controlling the pH in the precipitator in this range, i.e. about 3 to about 7, terephthalic acid will be formed from the potassium acid salt and will be caused to precipitate. Other aromatic carboxylic acids are more soluble than terephthalic acid and will remain in solution. A low pH, for example below about 3, in the precipitator is undesirable because this will cause impurities to co-precipitate with terephthalic acid, while a high pH, for example over about 7, is undesirable because insufficient precipitation of terephthalic acid will result, thereby reducing the yield.

The temperature in the precipitator must be controlled below the temperature at which significant product begins to dissolve. This temperature is about 5° to about 25° C. when the principal product is terephthalic acid. Precipitator 120 may be any type, such as a continuous stirred tank reactor.

Gases removed from separator 75 through line 77, which comprise carbon dioxide, can be used to maintain at least part of carbon dioxide atmosphere in the isomerization reactor 80. These gases are fed to reactor 80 through line 78 or vented through line 79. If gases from separator 75 contain free oxygen then the free oxygen must be removed or converted to carbon dioxide (not shown) before the gases are fed to isomerization reactor 80.

All of the products are removed from precipitator 120 through line 122 and enter filter 130. Filter 130 may be any type, such as a precoated revolving drum filter.

The solid product, terephthalic acid, is removed from filter 130 through line 131 and stored in storage vessel 135.

The liquids are separated from the solid terephthalic acid in filter 130 and the liquid is removed from the filter through line 132. If it is desired to remove more soluble carboxylic acids from the acid solution, then liquids in line 13 are fed to separator 140.

Separator 140 may be a liquid-liquid extraction apparatus. The separated carboxylic acids are removed from the separator 140 through line 152 and are fed to purifier 160. Purification of the carboxylic acid in purifier 160 may be by conventional means. The purified carboxylic acids are removed from the purifier 160 through line 162 and sent to storage vessel 170. The impurities, consisting principally of potassium salts and water soluble aromatic acids, are removed from purifier 160 through line 164. These impurities may be recycled to the autoclave.

In an alternate embodiment (not shown), if it is not desirable to remove the more soluble carboxylic acids from liquid stream 132, then stream 132 is fed directly to separator 190 instead of stream 142 for separation of acetic acid from potassium acetate. In this embodiment elements 140, 142, 152, 160, 162, 164, and 170 are omitted.

Returning to separator 140, stream 142, which does not contain the separated aromatic carboxylic acid but which contains potassium acetate and acetic acid, is fed to separator 190 for separation of acetic acid from potassium acetate. Acetic acid may be separated from potassium acetate in separator 190 by distillation or by steam distillation, or by solvent extraction or by other standard procedures.

The separated acetic acid is removed from separator 190 through line 194 and is recycled to precipitator 120 through line 126. Make-up acetic acid may be added to precipitator 120 through line 124.

Potassium acetate is removed from separator 190 through line 192 and enters reactor 200 whereupon it is treated with lime which is introduced to reactor 200 through line 196. The purpose of the lime treatment is to prevent buildup of sulfate in the recycle stream and thereby liberate potassium for recycle. Reactor 200 can be a continuous stirred tank reactor.

The product from reactor 200 is removed therefrom through line 202 and enters filter 210 whereupon calcium sulphate is separated as a solid from the liquid stream containing the dissolved potassium acetate. Filter 210 may be any type, such as a vacuum filter. Calcium sulphate is removed from filter 210 by line 212. The calcium sulphate may be used in the making of portland cement, gypsum or pool acid or disposed of by landfill. The potassium acetate stream is removed from filter 210 through line 214 and is recycled to mixer 20. Make-up potassium acetate may be added to mixer 20 through line 14.

Figure 2:
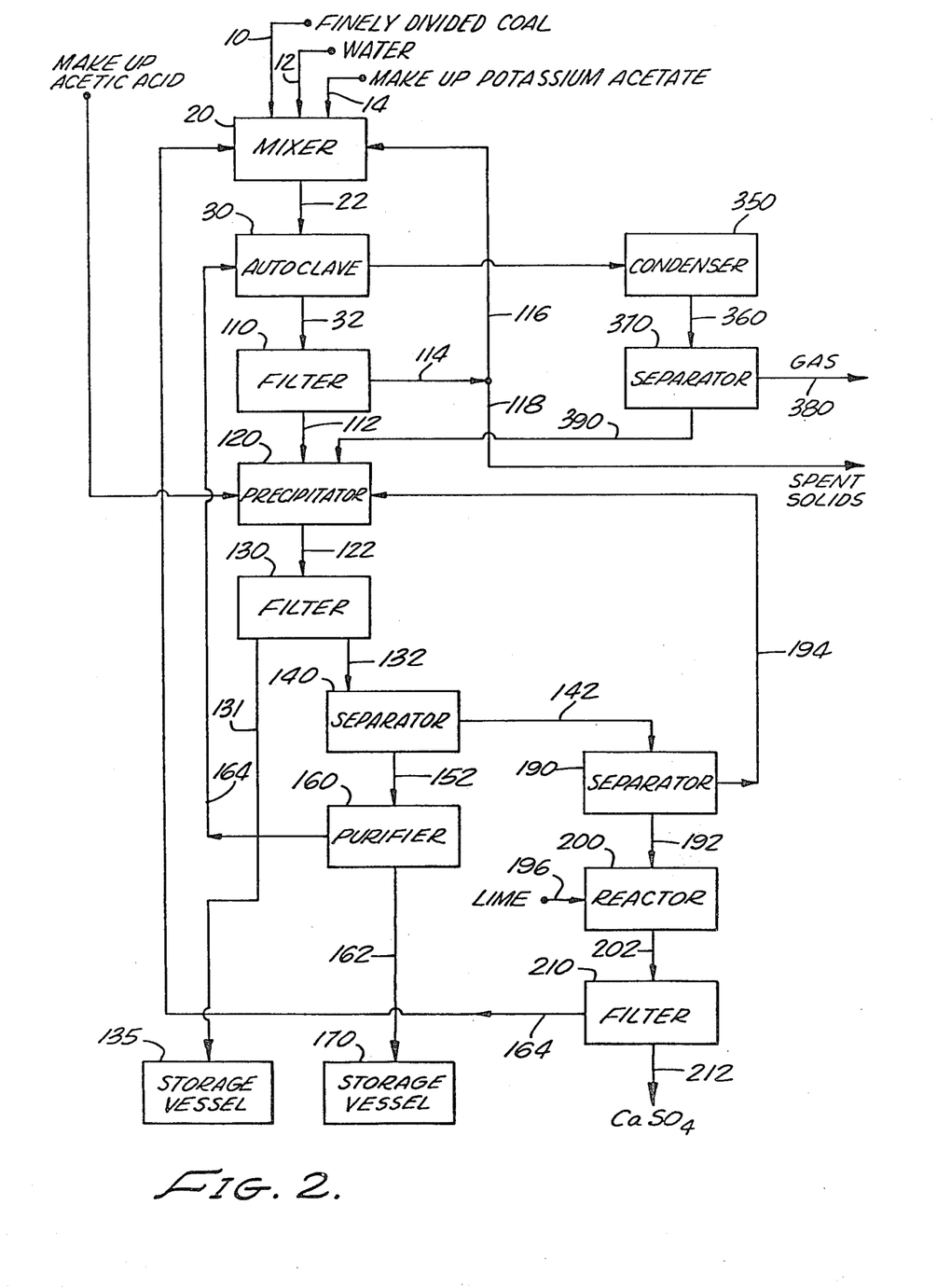
FIG. 2 is a schematic flow diagram for my process for the production of benzene carboxylic acid from coal.

Alternately, if there is no desire to produce isomerized carboxylic acids, stream 32 can be fed directly to filter 110 and the steps involving elements 40 through 102 are omitted. The alternate process is shown in FIG. 2. This process, although similar, still has considerable value because of the regeneration and recycling of potassium acetate, line 214, to mixer 20 or, alternately, to autoclave 30 (not shown). However, by eliminating the isomerization step, an aromatic carboxylic acid of different constituents is produced and the yield of terephthalic acid will be reduced. This carboxylic acid mixture is useful in detergent manufacturing.

In an especially preferred embodiment, the product from the isomerization reactor 80, preferably having been cooled in cooler 90, dissolved in dissolver 100 and filtered in filter 110 to remove undissolved solids is sent to a precipitator for treatment with carbon dioxide. in this embodiment, the precipitator is used to precipitate the monopotassium salt of terephthalic acid by treatment with carbon dioxide. Thus, the aqueous solution containing dipotassium terephthalate in stream 112 is treated in the precipitator with carbon dioxide to produce the monopotassium salt of terephthalic acid and potassium bicarbonate. In this embodiment, which is not shown in either FIGS. 1 or 2, acetic acid is not charged to the precipitator. The precipitator is maintained at a temperature below about 50° C., preferably below 30° C. and especially preferably at about 0° C. to enhance the dissolving of carbon dioxide in the solution.

The monopotassium salt of terephthalic acid, a precipitate, is separated from the aqueous solution of potassium bicarbonate in a separation zone which may be a filter. The separated monopotassium salt of terephthalic acid is then charged to a hydrolyzer where it is treated with water to form dipotassium terephthalate and terephthalic acid. The dipotassium terephthalate remains in solution while the terephthalic acid precipitates. The terephthalic acid may then be separated from the dipotassium terephthalate solution and the dipotasium terephthalate solution recycled to the precipitator above, or to dissolver 100, or treated in another zone. In either case, the dipotassium terephthalate is treated with carbon dioxide to convert the dipotassium terephthalate to monopotassium salt of terephthalic acid and additional potassium bicarbonate.

The monopotassium salt of terephthalic acid can be neutralized by other means, if desired, such as treatment with carbon dioxide or an acid such as acetic acid in an aqueous solution.

The potassium bicarbonate solution after separation from the monopotassium solid terephthalic acid can be recycled to mixer 20, or alternately to autoclave 30, as the water soluble reagent comprising a Group Ia or IIa metal. Preferably the potassium bicarbonate is converted to potassium carbonate by heating, and the potassium carbonate is recycled to mixer 20, or alternately to autoclave 30 as the water soluble reagent comprising a Group Ia or IIa metal. In this embodiment, the water soluble reagent comprising a Group Ia or IIa metal does not require the use of a formate, acetate or propionate of such metal.

Furthermore, in this embodiment the alkali metal reagent, which is potassium in the above description, is recovered and recycled in the proces. As can be seen, no conversion of the potassium benzene carboxylic acid salt prior to isomerization is required in the process. That is to say, it is not necessary to convert the potassium benzene carboxylic acid salt to a sodium benzene carboxylic acid salt, or vice versa, prior to isomerization.

Another advantage of this invention is that it is not necessary to prepare the salts in a separate zone apart from the oxidation zone since in this invention the salts are prepared directly in the oxidation zone.

Similarly, another advantage of this invention is that it is not necessary to convert the benzene carboxylic acid salts to their benzene carboxylic acids prior to the isomerization step.

Still another advantage of this invention is that after the aromatic material is oxidized in the presence of a first compound comprising a Group Ia or IIa metal to form a benzene carboxylic acid salt of the Group Ia or IIa metal, it is not necessary to convert the benzene carboxylic acid salt of the Group Ia or IIa metal to another benzene carboxylic acid salt of another Group Ia or IIa metal prior to isomerization.

Another advantage is that the reagent is regenerated by the process.

EXAMPLE I

Regeneration Of Reagent

The following is an example of the conversion of a benzene carboxylic acid with a metal acetate to a metal benzene carboxylate followed by the conversion of the metal benzene carboxylate by treating with an excess acetic acid to convert the metal benzene carboxylate to benzene carboxylic acid. (This corresponds to Step Nos. 30, 40, 50, 60, 120, 130, and 190 in FIG. 1.)

18.82 gr of dry reagent grade trimesic acid (1, 3, 5 benzene-tricarboxylic acid) was added to a flask together with 39.50 gr of potassium acetate and 300 gr of water. This mixture was boiled until all of the trimesic acid was dissolved. (This corresponds to the state found in autoclave 30 of FIG. 1.)

The mixture was then evaporated to dryness. It is estimated that at least 80% of the acid was converted to its potassium salt. (This corresponds to the state found in dryer 60 of FIG. 1.) The condensate consisted of acetic acid and water.

Three extractions of the acid salt took place using 80 $cm^3$ of a mixture containing 90% glacial acetic acid and 10% by weight of water for each extraction. Each extraction took place at 60° C. with stirring for 15 minutes. Each time the acetic acid water mixture containing newly formed potassium acetate was passed through a 50-60 ASTM sintered glass filter, with the newly formed trimesic acid remaining behind. (This corresponds to steps 120 and 130 in FIG. 1.)

The extract was evaporated to dryness by heating to 200° C. under vacuum. 37.53 gr of extract or 95% by weight of the original potassium acetate was recovered. The weight of the remaining dry trimesic acid was 20.22 gr. It thus contained the remaining potassium. (This corresponds to step 190 in FIG. 1.)

The fact that the reclaimed potassium acetate may contain some potassium trimesate and trimesic acid in this experiment is of no consequence to the process of this invention because it is intended that the reclaimed potassium acetate be recycled. However, should a higher reclamation factor be desired, the extraction with the acetic acid water mixture can be repeated with the results being predicted by a fractionation curve as used in distillation.

EXAMPLE II

Oxidation of Coal

About 28 gr of coal, 170 gr of potassium acetate, and 400 gr of water were charged to a stirred autoclave.

The mixture was treated with oxygen at a total pressure of 1700 psig at a temperature of 500° F. for 30 minutes with continuous stirring taking place.

The autoclave contents were analyzed and 12.8 gr of coal acids were found to be present. About 6.4 gr of this was benzene carboxylic acids, which represents a 28% yield on a dry ash free coal basis.

EXAMPLE III

Regeneration Of Reagent, Specifically Potassium Acetate

To demonstrate the regeneration of potassium acetate, the following experiment was carried out.

Pyromellitic acid, a typical constituent of coal acids, was used.

18.82 gr of pyromellitic acid were reacted with 39.5 gr of potassium acetate to give 30.4 gr of tetrapotassium pyromellate and an unmeasured amount of acetic acid. The acetic acid is recoverable by distillation. The salt was extracted with a water/acetic acid mixture, and 37.5 gr of potassium acetate was recovered.

The salt was converted back to pyromellitic acid. Thus, 95% potassium acetate was reclaimed after forming the potassium salt of pyromellitic acid.

EXAMPLE IV

Precipitation Of Aromatic Carboxylic Acid, Specifically Terephthalic Acid

A prepared solution of potassium terephthalate consisting of 10 gr of potassium terephthalate in 100 gr of water was treated with 100 ml of 6% acetic acid solution and immediately produced 6.7 gr of a white precipitate of terephthalic acid.

EXAMPLE V

Isomerization Of Coal Acids

About 9.3 gr of coal acids were converted to their corresponding potassium salts. 0.5 gr of cadmium oxide was thoroughly mixed with the salts. The mixture was then dried to remove moisture.

The mixture was charged to an autoclave which was pressurized to 130 psig with carbon dioxide. It was heated to 400° C. and maintained at that temperature for four hours while at 130 psig.

After cooling, the mixture was dissolved in boiling water and filtered to remove char containing the cadmium.

Upon acidification of the mixture with 100 ml of 6% acetic acid solution, a yield of 3.2 gr of terephthalic acid was obtained. This corresponds to a 36% yield from the coal acids.

EXAMPLE VI

Conversion Of Coal To Terephthalic Acid 100 gr potassium acetate and 30 gr of bituminous coal are mixed with 400 gr of water. The mixture is charged to an oxidation autoclave and heated to 260° C. Oxygen is slowly added to the autoclave until a total pressure of 1500 psig is achieved. A product gas consisting of carbon dioxide, steam, and acetic acid is periodically vented from the autoclave, and the autoclave is repressurized with oxygen to 1500 psig each time. After half an hour of treatment with oxygen, the autoclave contents are cooled to room temperature and discharged from the autoclave.

The oxidized mixture is dried by boiling until almost dry and the vapors condensed. A total of 407.6 gr of liquid condensate is collected by combining the condensate from the product gas and the drying operation. The total condensate comprises of 16.6 gr of acetic acid. The moist oxidized mixture is thoroughly dried under vacuum for three hours.

About 2.0 gr of cadmium iodide, as catalyst, is intimately mixed with the dried, oxidized mixture. The mixture is then charged to an isomerization autoclave and heated to 150° F. Remaining moisture is purged from the autoclave using dry carbon dioxide. The autoclave is heated to 395° C. for 2.5 hours with 600 psig of carbon dioxide pressure.

The autoclave is then cooled to room temperature. The solid material is removed from the autoclave and dissolved in 100 gr of hot water. The solution is filtered to remove char and solids.

The condensate from oxidization and drying steps, which contains acetic acid, is added to the solution. A precipitate of 10.2 gr of crude terephthalic acid is formed. The terephthalic acid precipitate is separated by filtration.

The filtrate, or mother liquor, is evaporated to form a condensate containing 0.9 gr of acetic acid dissolved in 450 gr of water. 102 gr of solid residue, containing 98.5 gr of potassium acetate is obtained. The solid residue is recycled to the next oxidation step.

The 450 gr of water is reduced in weight to 400 gr and 1.5 gr of makeup potassium carbonate is added, converting the remaining acetic acid in solution to potassium acetate. The solution is recycled to the oxidation step. It can be seen that nearly all of the original potassium acetate is recovered and recycled.

The following table summarizes the mass flows in Example VI.

| | |
|---|---|
| Weight of Coal | 30.0 gr |
| Weight of Potassium Acetate | 100.0 gr |
| Weight of Recovered Potassium Acetate | 98.5 gr |
| Weight of Unused Acetic Acid | 0.9 gr |
| Weight of Potassium Carbonate Required to Regenerate Potassium Acetate from Acetic Acid | 1.5 gr |

EXAMPLE VII

Conversion Of Coal Char To Terephthalic Acid 100 gr potassium acetate and 30 gr of coal char are mixed with 400 gr of water. The coal char is produced by pyrolyzing a bituminous coal at 1500° F. for 20 minutes in a fluidized bed reactor. The mixture is charged to an oxidation autoclave and heated to 260° C. Oxygen is slowly added to the autoclave until a total pressure of 1500 psig is achieved. A product gas consisting of carbon dioxide, steam, and acetic acid is periodically vented from the autoclave, and the autoclave is repressurized with oxygen to 1500 psig each time. After half an hour of treatment with oxygen, the autoclave contents are cooled to room temperature and discharged from the autoclave.

The oxidized mixture is dried by boiling until almost dry and the vapors condensed. A total of 407.6 gr of liquid condensate is collected by combining the condensate from the product gas and the drying operation. The total condensate comprises of 16.6 gr of acetic acid. The moist oxidized mixture is thoroughly dried under vacuum for three hours.

About 2.0 gr of cadmium iodide, as catalyst, is intimately mixed with the dried, oxidized mixture. The mixture is then charged to an isomerization autoclave and heated to 150° F. Remaining moisture is purged from the autoclave using dry carbon dioxide. The autoclave is heated to 395° C. for 2.5 hours with 600 psig of carbon dioxide pressure.

The autoclave is then cooled to room temperature. The solid material is removed from the autoclave and dissolved in 100 gr of hot water. The solution is filtered to remove char and solids.

The condensate from the oxidation and drying steps, which contains acetic acid, is added to the solution. A precipitate of 6.3 gr of crude terephthalic acid is formed. The terephthalic acid precipitate is separated by filtration.

The filtrate, or mother liquor, is evaporated to form a condensate containing 0.9 gr of acetic acid dissolved in 450 gr of water. 102 gr of solid residue, containing 98.5 gr of potassium acetate is obtained. The solid residue is recycled to the next oxidation step.

The 450 gr of water is reduced in weight to 400 gr and 1.5 gr of makeup potassium carbonate is added, converting the remaining acetic acid in solution to potassium acetate. The solution is recycled to the oxidation step. It can be seen that nearly all of the original potassium acetate is recovered and recycled.

The following table summarizes the mass flows in Example VII.

| | |
|---|---|
| Weight of Coal Char | 30.0 gr |
| Weight of Potassium Acetate | 100.0 gr |
| Weight of Recovered Potassium Acetate | 98.5 gr |
| Weight of Unused Acetic Acid | 0.9 gr |
| Weight of Potassium Carbonate Required to Regenerate Potassium Acetate from Acetic Acid | 1.5 gr |

EXAMPLE VIII

Conversion Of Coal Tar To Terephthalic Acid 100 gr potassium acetate and 30 gr of coal tar are mixed with 400 gr of water. The coal tar is produced by pyrolyzing a bituminous coal to 1500° F. for 20 minutes in a fluidized bed, cooling the product vapors, and recovering the condensed coal tar. The mixture is charged to an oxidation autoclave and heated to 260° C. Oxygen is slowly added to the autoclave until a total pressure of 1500 psig is achieved. A product gas consisting of carbon dioxide, steam, and acetic acid is periodically vented from the autoclave, and the autoclave is repressurized with oxygen to 1500 psig each time. After half an hour of treatment with oxygen, the autoclave contents are cooled to room temperature and discharged from the autoclave.

The oxidized mixture is dried by boiling until almost dry and the vapors condensed. A total of 407.6 gr of liquid condensate is collected by combining the condensate from the product gas and the drying operation. The total condensate comprises of 16.6 gr of acetic acid. The moist oxidized mixture is thoroughly dried under vacuum for three hours.

About 2.0 gr of cadmium iodide, as catalyst, is intimately mixed with the dried, oxidized mixture. The mixture is then charged to an isomerization autoclave and heated to 150° F. Remaining moisture is purged from the autoclave using dry carbon dioxide. The autoclave is heated to 395° C. for 2.5 hours with 600 psig of carbon dioxide pressure.

The autoclave is then cooled to room temperature. The solid material is removed from the autoclave and dissolved in 100 gr of hot water. The solution is filtered to remove char and solids.

The condensate from the oxidization and drying steps, which contains acetic acid, is added to the solution. A precipitate of 11.8 gr of crude terephthalic acid is formed. The terephthalic acid precipitate is separated by filtration.

The filtrate, or mother liquor, is evaporated to form a condensate containing 0.9 gr of acetic acid dissolved in 450 gr of water. 102 gr of solid residue, containing 98.5 gr of potassium acetate is obtained. The solid residue is recycled to the next oxidation step.

The 450 gr of water is reduced in weight to 400 gr and 1.5 gr of makeup potassium carbonate is added, converting the remaining acetic acid in solution to potassium acetate. The solution is recycled to the oxidation step. It can be seen that nearly all of the original potassium acetate is recovered and recycled.

The following table summarizes the mass flows in Example VIII.

| | |
|---|---|
| Weight of Coal Tar | 30.0 gr |
| Weight of Potassium Acetate | 100.0 gr |
| Weight of Recovered Potassium Acetate | 98.5 gr |
| Weight of Unused Acetic Acid | 0.9 gr |
| Weight of Potassium Carbonate Required to Regenerate Potassium Acetate from Acetic Acid | 1.5 gr |

EXAMPLE IX

Conversion Of Heavy Residual Oil To Terephthalic Acid 100 gr potassium acetate and 30 gr of heavy residual oil from a naphthenic crude oil are mixed with 400 gr of water. The mixture is charged to an oxidation autoclave and heated to 260° C. Oxygen is slowly added to the autoclave until a total pressure of 1500 psig is achieved. A product gas consisting of carbon dioxide, steam, and acetic acid is periodically vented from the autoclave, and the autoclave is repressurized with oxygen to 1500 psig each time. After half an hour of treatment with oxygen, the autoclave contents are cooled to room temperature and discharged from the autoclave.

The oxidized mixture is dried by boiling until almost dry and the vapors condensed. A total of 407.6 gr of liquid condensate is collected by combining the condensate from the product gas and the drying operation. The total condensate comprises of 16.6 gr of acetic acid. The moist oxidized mixture is thoroughly dried under vacuum for three hours.

About 2.0 gr of cadmium iodide, as catalyst, is intimately mixed with the dried, oxidized mixture. The mixture is then charged to an isomerization autoclave and heated to 150° F. Remaining moisture is purged from the autoclave using dry carbon dioxide. The autoclave is heated to 395° C. for 2.5 hours with 600 psig of carbon dioxide pressure.

The autoclave is then cooled to room temperature. The solid material is removed from the autoclave and dissolved in 100 gr of hot water. The solution is filtered to remove char and solids.

The condensate from the oxidization and drying steps, which contains acetic acid, is added to the solution. A precipitate of 3.8 gr of crude terephthalic acid is formed. The terephthalic acid precipitate is separated by filtration.

The filtrate, or mother liquor, is evaporated to form a condensate containing 0.9 gr of acetic acid dissolved in 450 gr of water. 102 gr of solid residue, containing 98.5 gr of potassium acetate is obtained. The solid residue is recycled to the next oxidation step.

The 450 gr of water is reduced in weight to 400 gr and 1.5 gr of makeup potassium carbonate is added, converting the remaining acetic acid in solution to potassium acetate. The solution is recycled to the oxidation step. It can be seen that nearly all of the original potassium acetate is recovered and recycled.

The following table summarizes the mass flows in Example IX.

| | |
|---|---|
| Weight of Heavy Residual Oil | 30.0 gr |
| Weight of Potassium Acetate | 100.0 gr |
| Weight of Recovered Potassium Acetate | 98.5 gr |
| Weight of Unused Acetic Acid | 0.9 gr |
| Weight of Potassium Carbonate Required to Regenerate Potassium Acetate from | |

| -continued | |
|---|---|
| Acetic Acid | 1.5 gr |

EXAMPLE X

Conversion Of Dipotassium Terephthalate To Terephthalic Acid Using Carbon Dioxide.

29 gr of dipotassium terephthalate were dissolved in 200 ml of hot deionized water and the solution was filtered to remove any insoluble solids. Carbon dioxide was bubbled through the solution as it was cooled in an ice bath. White crystals immediately began to form. After the suspension of crystals in the solution had cooled to a temperature of less than $-2°$ C. (28° F.) and let stand for thirty minutes, it was then vacuum filtered. The white needles on the filter were washed with ice water, dried in a vacuum oven, and weighed. Approximately 16.2 gr of precipitate were recovered. A sample was analyzed and found to have the composition:

| Element | % by Weight |
|---|---|
| C | 47.4 |
| H | 2.8 |
| K | 18.1 |
| O | 31.7 (by difference) |

Pure potassium hydrogen terephthalate has the following composition:

| Element | % by Weight |
|---|---|
| C | 47.0 |
| H | 2.5 |
| K | 19.2 |
| O | 31.3 |

Thus, the precipitate is potassium hydrogen terephthalate.

The potassium hydrogen terephthalate was then dissolved in 160 ml of water and boiled for 5 minutes. About 6.5 gr of terephthalic acid were recovered by filtering the solution. The solution, which contains dipotassium terephthalate, can be concentrated and recycled to the carbon dioxide precipitation step.

EXAMPLE XI

Conversion Of Dipotassium Terephthalate To Terephthalic Acid Using Carbon Dioxide 29 gr of dipotassium terephthalate were dissolved in 200 ml of hot deionized water and the solution was filtered to remove any insoluble solids. Carbon dioxide was then bubbled through the solution (cooled to 25° C.) in a pressure filtration apparatus at 800 psig. About 20 gr of potassium hydrogen terephthalate were recovered after filtration. This was then dissolved in 200 ml of water and boiled for five minutes. About 8.0 gr of terephthalic acid were recovered by filtration of the solution.

The process of the invention has been described generally and by example with reference of clarity and illustration only. It will be apparent to those skilled in the art from the foregoing that various modifications of the process and the materials disclosed herein can be made without departure from the spirit of the invention. Accordingly, the invention is not to be construed or limited to the specific embodiments illustrated, but only as defined in the following claims.

I claim:

1. A process for producing isomerized benzene carboxylic acid salt from aromatic materials comprising:
   a. treating a mixture of
      i. an aromatic material,
      ii. water, and
      iii. a water soluble reagent comprising a Group Ia or IIa metal, said reagent producing an alkaline solution by hydrolysis,
   with oxygen under conditions of pressure, elevated temperature, and reaction time sufficient to convert at least a portion of said aromatic material to benzene carboxylic acid salts of said Group Ia or IIa metal of said reagent, thereby producing a solution containing dissolved therein said benzene carboxylic acid salts;
   b. removing sufficient water from said solution so that said benzene carboxylic acid salts can be isomerized, thereby producing dried benzene carboxylic acid salts;
   c. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acis salts to benzene carboxylic acids prior to isomerizing said benzene carboxylic acid salts; and
   d. recovering said isomerized benzene carboxylic acid salt.

2. A process for producing isomerized benzene carboxylic acid salt from aromatic materials comprising:
   a. treating a mixture of
      i. an aromatic material selected from the group consisting of lignite, peat, coke and char,
      ii. water, and
      iii. a water soluble reagent comprising a Group Ia or IIa metal, said reagent producing an alkaline solution by hydrolysis,
   with oxygen under conditions sufficient to convert at least a portion of said aromatic material to benzene carboxylic acid salts of said Group Ia or IIa metal of said reagent, thereby producing a solution containing dissolved therein said benzene carboxylic acid salts;
   b. removing sufficient water from said solution so that said benzene carboxylic acid salts can be isomerized, thereby producing dried benzene carboxylic acid salts;
   c. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts; and
   d. recovering said isomerized benzene carboxylic acid salt.

3. A process for producing isomerized benzene carboxylic acid salt from aromatic materials comprising:
   a. treating a mixture of i. an aromatic material selected from the group consisting of petroleum residium, pitch, tar, oil shale, or oil from oil shale,
ii. water, and
iii. a water soluble reagent comprising a Group Ia or IIa metal, said reagent producing an alkaline solution by hydrolysis, with oxygen under conditions sufficient to convert at least a portion of said aromatic material to benzene carboxylic acid salts of said Group Ia or IIa metal of said reagent, thereby producing a solution containing dissolved therein said benzene carboxylic acid salts;
b. removing sufficient water from said solution so that said benzene carboxylic acid salts can be isomerized, thereby producing dried benzene carboxylic acid salts;
c. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts; and
d. recovering said isomerized benzene carboxylic acid salt.

4. A process for producing isomerized benzene carboxylic acid salt from coal comprising:
a. treating a mixture of
i. coal,
ii. water, and
iii. a water soluble reagent comprising a Group Ia or IIa metal, said reagent producing an alkaline solution by hydrolysis, with oxygen under conditions sufficient to convert at least a portiion of said coal to benzene carboxylic acid salts of said Group Ia or IIa metal of said reagent, thereby producing a solution containing dissolved therein said benzene carboxylic acid salts;
b. removing sufficient water from said solution so that said benzene carboxylic acid salts can be isomerized, thereby producing dried benzene carboxylic acid salts;
c. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts; and
d. recovering said isomerized benzene carboxylic acid salt.

5. A process for producing isomerized benzene carboxylic acid from aromatic materials comprising:
a. treating a mixture of
i. an aromatic material,
ii. water, and
iii. a water soluble reagent comprising a Group Ia or IIa metal, said reagent producing an alkaline solution by hydrolysis, with oxygen under conditions of pressure, elevated temperature, and reaction time sufficient to convert at least a portion of said aromatic material to benzene carboxylic acid salts of said Group Ia or IIa metal of said reagent, thereby producing a solution containing dissolved therein said benzene carboxylic acid salts;
b. removing sufficient water from said solution so that said benzene carboxylic acid salts can be isomerized, thereby producing dried benzene carboxylic acid salts;
c. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts;
d. converting said isomerized benzene carboxylic acid salt to isomerized benzene carboxylic acid; and
e. recovering said isomerized benzene carboxylic acid.

6. A process for producing isomerized benzene carboxylic acid from aromatic materials comprising:
a. treating a mixture of
i. an aromatic material selected from the group consisting of lignite, peat, coke and char,
ii. water, and
iii. a water soluble reagent comprising a Group Ia or IIa metal, said reagent producing an alkaline solution by hydrolysis, with oxygen under conditions sufficient to convert at least a portion of said aromatic material to benzene carboxylic acid salts of said Group Ia or IIa metal of said reagent, thereby producing a solution containing dissolved therein said benzene carboxylic acid salts; b. removing sufficient water from said solution so that said benzene carboxylic acid salts can be isomerized, thereby producing dried benzene carboxylic acid salts;
c. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts;
d. converting said isomerized benzene carboxylic acid salt to isomerized benzene carboxylic acid; and
e. recovering said isomerized benzene carboxylic acid.

7. A process for producing isomerized benzene carboxylic acid from aromatic materials comprising:
a. treating a mixture of
i. an aromatic material selected from the group consisting of petroleum residium, pitch, tar, oil shale, or oil from oil shale,
ii. water, and
iii. a water soluble reagent comprising a Group Ia or IIa metal, said reagent producing an alkaline solution by hydrolysis, with oxygen under conditions sufficient to convert at least a portion of said aromatic material to benzene carboxylic acid salts of said Group Ia or IIa metal of said reagent, thereby producing a solution containing dissolved therein said benzene carboxylic acid salts;
b. removing sufficient water from said solution so that said benzene carboxylic acid salts can be isomerized, thereby producing dried benzene carboxylic acid salts;
c. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts;
d. converting said isomerized benzene carboxylic acid salt to isomerized benzene carboxylic acid; and
e. recovering said isomerized benzene carboxylic acid.

8. A process for producing isomerized benzene carboxylic acid from coal comprising:
a. treating a mixture of
i. coal,
ii. water, and
iii. a water soluble reagent comprising a Group Ia or IIa metal, said reagent producing an alkaline solution by hydrolysis, with oxygen under conditions sufficient to convert at least a portion of said coal to benzene carboxylic acid salts of said Group Ia or IIa metal of said reagent, thereby producing a solution containing dissolved therein said benzene carboxylic acid salts;
b. removing sufficient water from said solution so that said benzene carboxylic acid salts can be isomerized, thereby producing dried benzene carboxylic acid salts;
c. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts;
d. converting said isomerized benzene carboxylic acid salt to isomerized benzene carboxylic acid; and
e. recovering said isomerized benzene carboxylic acid.

9. A process for producing isomerized benzene carboxylic acid from aromatic materials comprising:
a. treating in an oxidation zone a mixture of
i. an aromatic material,
ii. water, and
iii. a water soluble reagent comprising a Group Ia or IIa metal, said reagent producing an alkaline solution by hydrolysis,
with oxygen under conditions of pressure, elevated temperature, and reaction time sufficient to convert at least a portion of said aromatic material to benzene carboxylic acid salts of said Group Ia or IIa metal of said reagent, thereby producing a first solution containing dissolved therein said benzene carboxylic acid salts;
b. separating undissolved solids from said first solution to produce an essentially solids-free first solution;
c. removing sufficient water from said essentially solids-free first solution so that said benzene carboxylic acid salts can be isomerized, thereby producing dried benzene carboxylic acid salts;
d. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts;
e. converting said isomerized benzene carboxylic acid salt to isomerized benzene carboxylic acid and a second solution comprising a cation of said Group Ia or IIa metal of said reagent;
f. recovering said isomerized benzene carboxylic acid;
g. regenerating from said second solution said reagent comprising said Group Ia or IIa metal; and
h. recycling said reagent comprising said Group Ia or IIa metal thusly regenerated to said oxidation zone to supply a large portion of said reagent required for producing said benzene carboxylic acid salts.

10. A process for producing isomerized benzene carboxylic acid from aromatic materials comprising:
a. treating in an oxidation zone a mixture of
i. an aromatic material selected from the group consisting of lignite, peat, coke and char,
ii. water, and
iii. a water soluble reagent comprising a Group Ia or IIa metal, said reagent producing an alkaline solution by hydrolysis,
with oxygen under conditions sufficient to convert at least a portion of said aromatic material to benzene carboxylic acid salts of said Group Ia or IIa metal of said reagent, thereby producing a first solution containing dissolved therein said benzene carboxylic acid salts;
b. separating undissolved solids from said first solution to produce an essentially solids-free first solution;
c. removing sufficient water from said essentially solids-free first solution so that said benzene carboxylic acid salts can be isomerized, thereby producing dried benzene carboxylic acid salts;
d. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts;
e. converting said isomerized benzene carboxylic acid salt to isomerized benzene carboxylic acid and a second solution comprising a cation of said Group Ia or IIa metal of said reagent;
f. recovering said isomerized benzene carboxylic acid;
g. regenerating from said second solution said reagent comprising said Group Ia or IIa metal; and h. recycling said reagent comprising said Group Ia or IIa metal thusly regenerated to said oxidation zone to supply a large portion of said reagent required for producing said benzene carboxylic acid salts.

11. A process for producing isomerized benzene carboxylic acid from aromatic materials comprising:
   a. treating in an oxidation zone a mixture of
      i. an aromatic material selected from the group consisting of petroleum residuum, pitch, tar, oil shale, or oil from oil shale,
      ii. water, and
      iii. a water soluble reagent comprising a Group Ia or IIa metal, said reagent producing an alkaline solution by hydrolysis,
   with oxygen under conditions sufficient to convert at least a portion of said aromatic material to benzene carboxylic acid salts of said Group Ia or IIa metal of said reagent, thereby producing a first solution containing dissolved therein said benzene carboxylic acid salts;
   b. separating undissolved solids from said first solution to produce an essentially solids-free first solution;
   c. removing sufficient water from said essentially solids-free first solution so that said benzene carboxylic acid salts can be isomerized, thereby producing dried benzene carboxylic acid salts;
   d. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts;
   e. converting said isomerized benzene carboxylic acid salt to isomerized benzene carboxylic acid and a second solution containing a cation of said Group Ia or IIa metal of said reagent;
   f. recovering said isomerized benzene carboxylic acid;
   g. regenerating from said second solution said reagent comprising said Group Ia or IIa metal; and
   h. recycling said reagent comprising said Group Ia or IIa metal thusly regenerated to said oxidation zone to supply a large portion of said reagent required for producing said benzene carboxylic acid salts.

12. A process for producing isomerized benzene carboxylic acid from coal comprising:
   a. treating in an oxidation zone a mixture of
      i. coal,
      ii. water, and
      iii. a water soluble reagent comprising a Group Ia or IIa metal, said reagent producing an alkaline solution by hydrolysis,
   with oxygen under conditions sufficient to convert at least a portion of said coal to benzene carboxylic acid salts of said Group Ia or IIa metal of said reagent, thereby producing a first solution containing dissolved therein said benzene carboxylic acid salts;
   b. separating undissolved solids from said first solution to produce an essentially solids-free first solution;
   c. removing sufficient water from said essentially solids-free first solution so that said benzene carboxylic acid salts can be isomerized, thereby producing dried benzene carboxylic acid salts;
   d. isomerizing said dried benzene carboxylic acid salts by heating to produce an isomerized benzene carboxylic acid salt without converting said benzene carboxylic acid salts to benzene carboxylic acid salts of a different Group Ia or IIa metal prior to isomerizing said benzene carboxylic acid salts, and without converting said benzene carboxylic acid salts to benzene carboxylic acids prior to isomerizing said benzene carboxylic acid salts;
   e. converting said isomerized benzene carboxylic acid salt to isomerized benzene carboxylic acid and a second solution containing a cation of said Group Ia or IIa metal of said reagent;
   f. recovering said isomerized benzene carboxylic acid;
   g. regenerating from said solution said reagent comprising said Group Ia or IIa metal; and
   h. recycling said reagent comprising said Group Ia or IIa metal thusly regenerated to said oxidation zone to supply a large portion of said reagent required for producing said benzene carboxylic acid salts.

13. The process of claim 1, 2, 3 or 4 wherein said isomerized benzene carboxylic acid salt comprises dipotassium terephthalate.

14. The process of claim 1, 2, 3 or 4 wherein said water soluble reagent is potassium carbonate.

15. The process of claim 1, 2, 3 or 4 wherein said isomerized benzene carboxylic acid salt comprises dipotassium terephthalate and said water soluble reagent is potassium carbonate.

16. The process of claim 5, 6, 7, 8, 9, 10, 11 or 12 wherein said isomerized benzene carboxylic acid comprises terephthalic acid.

17. The process of claim 5, 6, 7, 8, 9, 10, 11 or 12 wherein said water soluble reagent is potassium carbonate.

18. The process of claim 5, 6, 7, 8, 9, 10, 11 or 12 wherein said isomerized benzene carboxylic acid comprises terephthalic acid and said water soluble reagent is potassium carbonate.

19. A process for producing terephthalic acid from coal comprising:
   a. treating in an oxidation zone a mixture of
      i. finely divided coal,
      ii. water, and
      iii. potassium carbonate,
   with oxygen at an oxidation temperature of from about 200° to about 350° C., at an oxidation pressure of from about 250 psig to about 2000 psig, and for an average residence time of treatment with oxygen of from about 10 minutes to about 3 hours, to convert said coal to water soluble potassium benzene carboxylic acid salts, and thereby producing carbon dioxide and a first solution containing dissolved therein said water soluble potassium benzene carboxylic acid salts;
   b. removing a gaseous stream comprising said carbon dioxide from said oxidation zone;
   c. separating undissolved solids from said first solution to produce an essentially solids-free first solution;
   d. removing sufficient water from said essentially solids-free first solution so that said water soluble potassium benzene carboxylic acid salts can be isomerized, thereby producing a dried potassium benzene carboxylic acid salt mixture;

e. isomerizing said dried potassium benzene carboxylic acid salt mixture by heating under an atmosphere comprising carbon dioxide to produce dipotassium terephthalic acid salt without converting said potassium benzene carboxylic acid salt mixture to a benzene carboxylic acid salt mixture of a different Group Ia or IIa metal than potassium prior to isomerizing said potassium benzene carboxylic acid salt mixture, and without converting said potassium benzene carboxylic acid salt mixture to a mixture of benzene carboxylic acids prior to isomerizing said potassium benzene carboxylic acid salt mixture;

f. utilizing a portion of said gaseous stream comprising said carbon dioxide to form said atmosphere comprising carbon dioxide in said isomerization zone;

g. dissolving said dipotassium terephthalic acid salt in a first dipotassium terephthalate solution to produce a second dipotassium terephthalate solution;

h. separating undissolved solids in said second dipotassium terephthalate solution from said solution, thereby producing an essentially solids-free second dipotassium terephthalate solution;

i. treating said essentially solids-free second dipotassium terephthalate solution in a precipitation zone with carbon dioxide to produce and precipitate monopotassium terephthalate and to produce a potassium bicarbonate solution;

j. separating said precipitated monopotassium terephthalate from said potassium bicarbonate solution, thereby producing a separated precipitated monopotassium terephthalate and a separated potassium bicarbonate solution;

k. converting said separated potassium bicarbonate solution to a potassium carbonate solution;

l. utilizing said potassium carbonate solution as at least a large portion of said potassium carbonate and said water used in said oxidation zone;

m. treating said separated precipitated monopotassium terephthalate with water under conditions sufficient to produce and precipitate terephthalic acid and to produce a third dipotassium terephthalate solution; and n. separating said precipitated terephthalic acid from said third potassium terephthalate solution, thereby producing a terephthalic acid product and a separated third dipotassium terephthalate solution.

20. The process of claim 19 further comprising utilizing said separated third dipotassium terephthalate solution to make at least a portion of said second dipotassium terephthalate solution used in said precipitation zone.

21. The process of claim 19 wherein said coal is a bituminous coal.

22. The process of claim 21 wherein said isomerizing of said dried potassium benzene carboxylic acid salt mixture is conducted in the presence of an isomerization catalyst.

23. The process of claim 22 wherein said isomerization catalyst is selected from the group consisting of cadmium benzoate and cadmium iodide.

* * * * *